United States Patent
Talbot

(10) Patent No.: US 10,117,658 B2
(45) Date of Patent: Nov. 6, 2018

(54) SURGICAL JIG

(71) Applicant: Trochlear Pty Ltd, Heidelberg, Victoria (AU)

(72) Inventor: Simon Talbot, Heidelberg (AU)

(73) Assignee: TROCHLEAR PTY LTD, Heidelberg, Victoria (AU)

( * ) Notice: Subject to any disclaimer, the term of this patent is extended or adjusted under 35 U.S.C. 154(b) by 308 days.

(21) Appl. No.: 15/021,482

(22) PCT Filed: Sep. 9, 2014

(86) PCT No.: PCT/AU2014/050220
§ 371 (c)(1),
(2) Date: Mar. 11, 2016

(87) PCT Pub. No.: WO2015/035466
PCT Pub. Date: Mar. 19, 2015

(65) Prior Publication Data
US 2016/0220263 A1    Aug. 4, 2016

(30) Foreign Application Priority Data

Sep. 12, 2013  (AU) .................................. 2013903514

(51) Int. Cl.
*A61B 17/17* (2006.01)
*A61B 17/15* (2006.01)
*A61B 34/20* (2016.01)

(52) U.S. Cl.
CPC ........ *A61B 17/1764* (2013.01); *A61B 17/155* (2013.01); *A61B 17/1717* (2013.01); *A61B 2034/2068* (2016.02)

(58) Field of Classification Search
CPC ............ A61B 17/1764; A61B 17/1717; A61B 17/155
See application file for complete search history.

(56) References Cited

U.S. PATENT DOCUMENTS

| | | | |
|---|---|---|---|
| 4,722,330 A | 2/1988 | Russell et al. | |
| 5,624,444 A | 4/1997 | Wixon et al. | |
| 5,658,293 A | 8/1997 | Vanlaningham | |

(Continued)

FOREIGN PATENT DOCUMENTS

| | | |
|---|---|---|
| EP | 0243109 | 10/1987 |
| EP | 0661023 | 7/1995 |

OTHER PUBLICATIONS

International Search Report and Written Opinion for Application No. PCT/AU2014/050220, dated Jan. 13, 2015, 11 pages.

(Continued)

*Primary Examiner* — Christian Sevilla
(74) *Attorney, Agent, or Firm* — McDermott Will & Emery LLP

(57) ABSTRACT

A method and a surgical alignment system for use in the positioning of a prosthetic component on or in a bone of a subject. The system includes an intramedullary member and a jig member which are connectable to each other to position the jig member relative to the intramedullary member in a sagittal orientation. The jig 5 member includes an elongate arm and the jig member is moveable in an axial plane and at least rotatable in a coronal plane relative to the intramedullary member to align the elongate arm with the bony landmark.

14 Claims, 8 Drawing Sheets

(56) References Cited

U.S. PATENT DOCUMENTS

| | | | |
|---|---|---|---|
| 5,769,855 A * | 6/1998 | Bertin | A61B 17/154 606/87 |
| 5,830,216 A * | 11/1998 | Insall | A61B 17/155 606/87 |
| 6,056,756 A | 5/2000 | Eng et al. | |
| 2004/0153084 A1 | 8/2004 | Haney et al. | |

OTHER PUBLICATIONS

Extended European Search Report from European Patent Application No. 14844645.3, dated May 19, 2017.

* cited by examiner

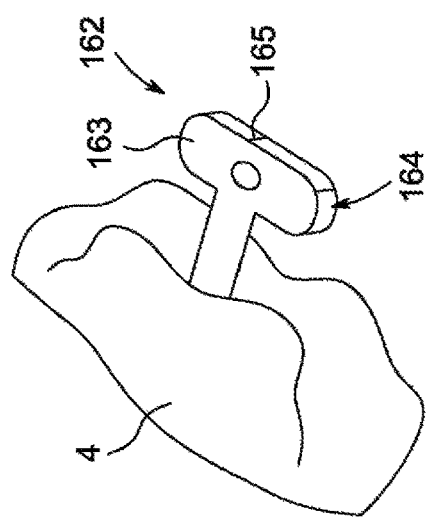
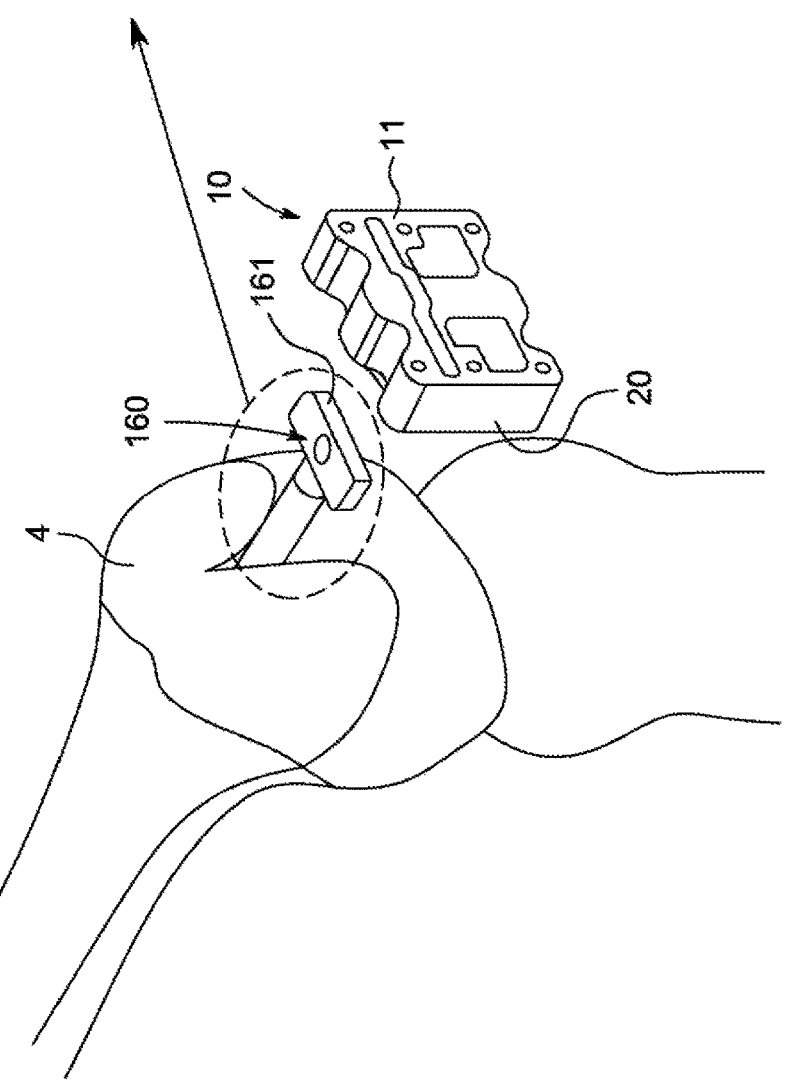

SURGICAL JIG

CROSS-REFERENCE TO RELATED APPLICATIONS

The present application is a national stage application, under 35 U.S.C. § 371, of International Application No. PCT/AU2014/050220, filed on Sep. 9, 2014, which claims the benefit of and priority from Australian provisional patent application no. 2013903514, filed on Sep. 12, 2013, the content of which is incorporated herein by reference.

FIELD

The present disclosure relates to devices and methods to enable optimal alignment of prosthetic components in the field of orthopaedics.

BACKGROUND

Replacement of various joints is becoming increasing common due to a longer life expectancy leading to the likelihood of greater wear and tear and damage to our joints. Particularly, hip and knee replacement surgeries are increasing dramatically in the over 65 cohort of the population.

In all cases, it is critically important to not only replace a bony portion with a correctly sized prosthesis but it is also vital for patient comfort and to prevent further complications to achieve the correct orientation of a prosthetic component. A successful knee arthroplasty will largely depend upon the proper alignment of the prosthetic components. For example, abnormal valgus or varus alignment has been reported as a cause of implant loosening. Further, incorrect femoral rotational alignment may be a major cause of patella-femoral complications, tibio-femoral instability and early failure.

To achieve an optimal alignment of a prosthesis such as a femoral prosthetic component, surgeons reference certain landmarks on the bone. For achieving the correct rotational alignment of the femoral component, the anterior cut of the femur must be correct and this is often achieved by referencing one or more of the posterior condylar axis, the anterior-posterior axis (also known as Whiteside's line which involves the identification of one anterior point and one posterior point in the trochlea groove to produce an axis) or the Sulcus Line (which is a version of the anterio-posterior axis which involves the identification of multiple points along the trochlea groove and thereby allows for orientation along the coronal axis of the trochlea groove) and the trans-epicondylar axis (TEA) which a line running from the medial and epicondylar sulcus and the lateral epicondyle.

It has been shown that aligning the femoral component with the TEA optimises patella-femoral tracking and approximates the flexion-extension axis of the knee. However, in practice, it is often difficult to accurately identify the TEA and one option is to identify and mark the Sulcus line which is taken to be perpendicular to the TEA.

Several problems have been encountered in accurately marking the Sulcus line, however and the variance is substantial depending upon the landmarks selected and the angle at which the line is viewed. Additional error is produced by current techniques which translate the vertical Sulcus line into a horizontal line drawn across the femoral condyles for alignment of the cutting blocks. This geometrical error is accentuated when the femoral condylar surface is not perpendicular to the coronal axis of the Sulcus Line.

There is a need, therefore, to address the deficiencies of the prior art and provide a means to accurately utilise the Sulcus line to allow a surgeon to accurately position a prosthetic knee component for optimal rotational alignment.

SUMMARY

In a first aspect, there is provided a surgical alignment system for use in positioning of a prosthetic component on or in a bone of a subject; said system including:
an intramedullary member;
a jig member, said intramedullary member and said jig member connectable to each other to substantially position the jig member relative to the intramedullary member in a sagittal orientation, said jig member including;
an elongate arm configured to align with a bony landmark of said bone; wherein
the jig member is moveable in an axial plane and at least rotatable in a coronal plane relative to the intramedullary member to substantially align the elongate arm with the bony landmark.

In a further aspect, there is provided a method for positioning a prosthetic component on or in a bone of a subject, said method including:
inserting an intramedullary member into the bone;
connecting a jig member to said intramedullary member to substantially position the jig member relative to the intramedullary member in a sagittal orientation, said jig member including an elongate arm configured to align with a bony landmark of said bone;
aligning the elongate arm with the bony landmark wherein the jig member is moveable in an axial plane and at least rotatable in a coronal plane relative to the intramedullary member to substantially align the elongate arm with the bony landmark as the elongate arm is aligned with the bony landmark.

In another aspect, there is provided a surgical alignment system for use in positioning of a prosthetic component on or in a bone of a subject, said system for use with a computer assisted navigation alignment system and including:
a bone marker member;
a jig member, said bone marker member and said jig member connectable to each other to substantially position the jig member relative to the bone marker member in a sagittal orientation, said jig member including;
an elongate arm configured to align with a bony landmark of said bone; wherein
the jig member is moveable in an axial plane and at least rotatable in a coronal plane relative to the bone marker member to substantially align the elongate arm with the bony landmark.

In this aspect, the bone marker may replace the intramedullary member. The bone marker member may be positioned in the bone. In this regard, the bone marker member may include a pin for insertion into the bone at a particular sagittal alignment. The bone marker member may further include a connector member to connect with the jig member.

The bone marker member may be positioned by computer assisted navigation to provide a sagittal alignment for a planned cut of the bone. Alternatively, the bone marker member may be positioned using a further alignment jig.

In a further embodiment, the jig member includes a main body having a bone facing surface and an opposite surface. The main body may include at least two holes therein, the holes configured to receive a pin or screw or other like member. Typically, pins are drilled through the holes and into the bone to provide marker holes in the bone.

In one embodiment, the bony landmark comprises the Sulcus line on a femur of a subject. The Sulcus line is considered to comprise a line drawn along multiple points in the depth of the trochlea sulcus extending from the deepest part of the trochlear groove anteriorly to the centre of the intercondylar notch posteriorly of the femur.

The elongate arm of the present disclosure is configured to generally align with the Sulcus line. In this regard, said elongate arm may comprise a first end connectable to the main body of the jig member.

The elongate arm may form an arcuate body which extends upwardly and outwardly from the jig member to a distal end. The distal end may be substantially rounded.

Further, the elongate arm may taper in width along its length from the first end to said distal end.

The elongate arm is typically removably connectable to the jig member.

In one embodiment, the main body of the jig member has a longitudinal or main axis and a transverse axis. The jig member may comprise one or more apertures and/or slots which extend from the bone facing surface to the opposite surface. In one embodiment, the main body of the jig member includes an elongate slot to receive a proximal portion of the elongate arm adjacent to the first end of the elongate arm. The elongate slot may be formed in the opposite surface of the main body and may extend longitudinally. The slot may be sized to provide substantially a friction fit for the proximal portion of the elongate arm to secure the arm therein for use. Other means of attachment of the elongate arm to the jig member include a snap fit connection. The main body may further include a stop member to receive the first end of the elongate arm and thus prevent it slipping out of the slot.

The elongate arm is typically made from a substantially lightweight material. Examples include a lightweight metal or alloy or a polyurethane material. Typically, the elongate arm is made from stainless steel. The main body may be made from a metal or metal alloy.

Any one or all of the intramedullary member, the jig member or the elongate arm may be manufactured from a range of biocompatible materials. The material may be sterilisable using a variety of sterilization techniques. Alternatively, intramedullary member, the jig member or the elongate arm may be disposable after a single use. In one embodiment, the material may be selected from medical grade stainless steel, medical grade aluminium or titanium alloy, medical grade plastics such as high density polyethylene, polypropylene, acrylic or polycarbonate.

The main body of the jig member may further include a transversely extending slot. The transversely extending slot may receive at least a portion of the intramedullary member therein. In an embodiment wherein the intramedullary member is replaced with a bone marker member, the transversely extending slot may receive at least a portion of the bone marker member therein.

The intramedullary member may include an elongate member which extends from a proximal end to a distal end and wherein said distal end is configured for introduction into a bone and said proximal end is configured to extend outwardly from said bone.

The proximal end of the intramedullary member may form a substantially flattened end and may be sized to fit at least partially within the transversely extending slot of the main body of the jig member. In one embodiment, the proximal end portion comprises a paddle member which is sized to slide into a transversely extending slot of the jig member. The paddle member may be sized such that is moveable in the transversely extending slot along a transverse axis relative to the main body.

The intramedullary member including the paddle member may be substantially rotatable in a coronal plane relative to a bone in which it may be positioned. As such, when the jig main body and the intramedullary member are connected to one another, the main body of the jig member may be at least partially rotationally moveable in the coronal plane.

The rotational movement in the coronal plane and the movement of the paddle in a transverse plane may be effected to facilitate orientation of the attached elongate arm relative to the bony landmark.

In a procedure, having already positioned the main body relative to the intramedullary member or bone marker member in a sagittal plane, a user is substantially prevented from making a potential error causing movement of the main body of the jig member in this plane. Such potential errors may result from the angle of vision of the Sulcus line and thus lead to geometrical errors in marking the Sulcus line on to the distal femoral condylar surface or on to the planned distal femoral bone cut in circumstances in which there is a difference between the coronal alignment of the Sulcus line and the distal femoral condylar surface or the proposed distal femoral cut.

The jig member may be used in a method wherein a surgeon performs the anterior cut of a femur first. Alternatively, the jig member may be used in a method wherein the distal femoral cut is made first.

In a method wherein the anterior cut is performed first, the jig member may be pinned to the femoral bone. A separate cutting block may then be connected to the jig member directly to align the anterior cut with the jig member. Alternatively, a surgeon may mark pin holes into the femoral bone and then remove the jig member. Said pin holes may then be used to orientate a separate anterior cutting block.

To perform the distal femoral cut, the jig member may be pinned to the femoral bone and pins may be drilled through the femoral bone. The jig member may then be completely removed and the distal cut made. The pinholes that were drilled through the jig member may then be identified on the distal femoral cut surface and used to orientate anterior and/or posterior femoral cutting blocks.

By orientating the jig member along the coronal axis of the Sulcus line and by removing sagittal variation from the planned distal femoral cut, the rotational alignment of the trochlea groove can be transferred in a geometrically valid manner onto either the distal femoral condyles or the planned distal femoral cut(s) by way of the pin holes formed using the jig member, said pin holes inserted at an angle which is perpendicular to the main body of the jig member.

The pin holes in the bone are typically a representation of the rotational alignment of the trochlea groove which can be projected onto any surface with the same sagittal alignment. Therefore, they may be used as a reference point on the distal femoral condyles or on the planned distal femoral cut. Once the distal femoral cut is made these pin holes may be identified and represent the rotational alignment of the trochlea groove. This may allow an accurate representation of the Sulcus line for use in a distal cut first method and also allow the direct comparison with other landmarks such as the anatomical epicondylar axis, the surgical epicondylar axis and the posterior condylar axis, and other techniques such as the tibia-first gap balancing technique.

In total knee replacement surgery, the disclosed apparatus, methods and systems provide a main body of a jig member which, while rotatable in a coronal plane and moveable in a transverse plane as discussed, the angle of view for a surgeon is perpendicular to the sagittal plane of a proposed distal femoral cut. By substantially fixing this view, the jig member and the system prevents the introduction of geometrical errors due to incorrect positioning of the main body of the jig member in the sagittal plane.

As noted above, the jig member of the present disclosure may also be used with a computer navigation system. In this embodiment, the bone marker member is set by computer assisted navigation in a manner to set the sagittal alignment of a cutting block. The bone marker member may comprise, as noted, a pin and a paddle member wherein the paddle member is receivable in the transversely extending slot of the main body of the jig member. As such, as the elongate arm is positioned relative to the bony landmark, the main body of the jig member is translationally moveable relative to the bone marker member in a transverse plane. The bone marker member, as with the intramedullary member, may be rotatable in the coronal plane and by its connection with the main body, said main body may be similarly rotatable in the coronal plane. In all embodiments, the ultimate alignment of a cutting block is set in the sagittal plane by the bone marker member of intramedullary member.

The bone marker member may be inserted into a centre point of the femur, perpendicular to the planned sagittal cut, using either direct computer assisted navigation or with reference to a computer assisted navigated distal cutting block.

BRIEF DESCRIPTION OF THE DRAWINGS

FIG. 4 is a further view showing an intramedullary rod in the femur and positioning of the present jig member;

FIG. 5 is an exploded view of the end of the intramedullary rod member of FIG. 4;

EXEMPLARY DESCRIPTION OF ONE EMBODIMENT OF THE DISCLOSURE

During total knee replacement a surgeon aims to achieve optimal alignment of the femoral, tibial and patellar components. Careful alignment will reduce both the mechanical stress placed on the bearing surfaces and the shear stress on the bone/prosthesis or bone/cement/prosthesis interfaces. Good alignment also helps to balance the forces transmitted to the soft-tissue envelope, which is essential for proper functioning of the joint.

Figure 1:
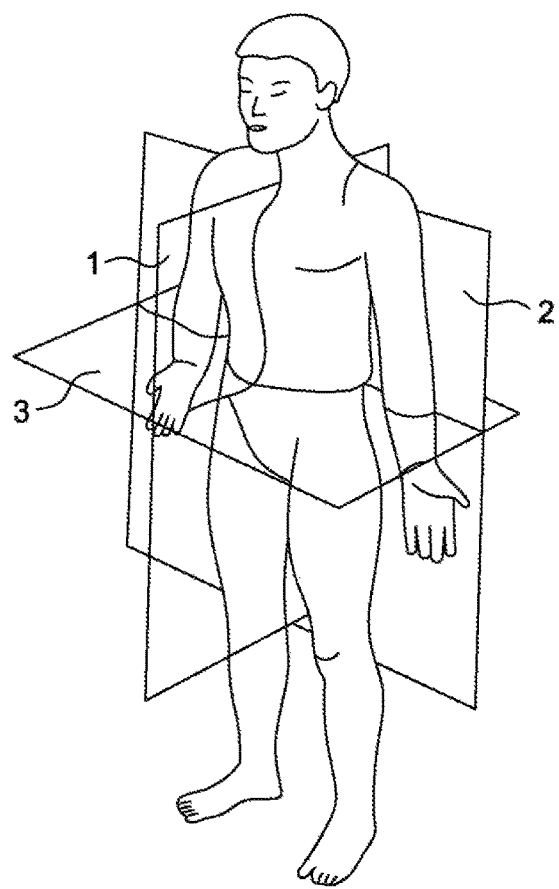
FIG. 1 is a diagram showing the planes of a body.
Figure 2:
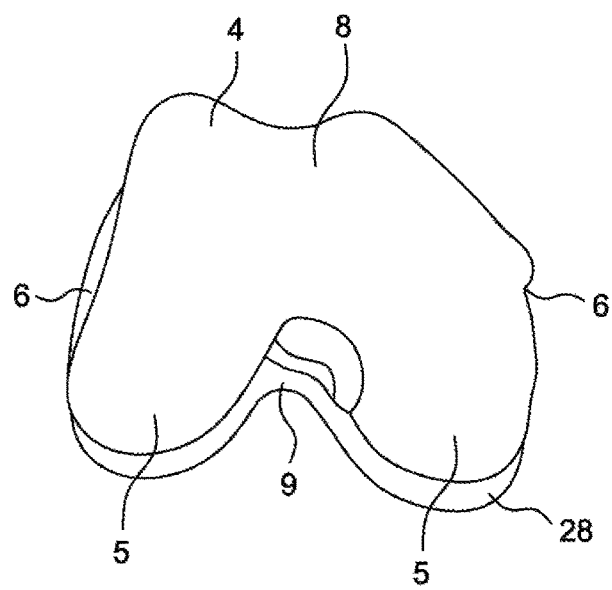
FIG. 2 is a view of the distal end of a femur showing landmarks and axes.
Figure 3:
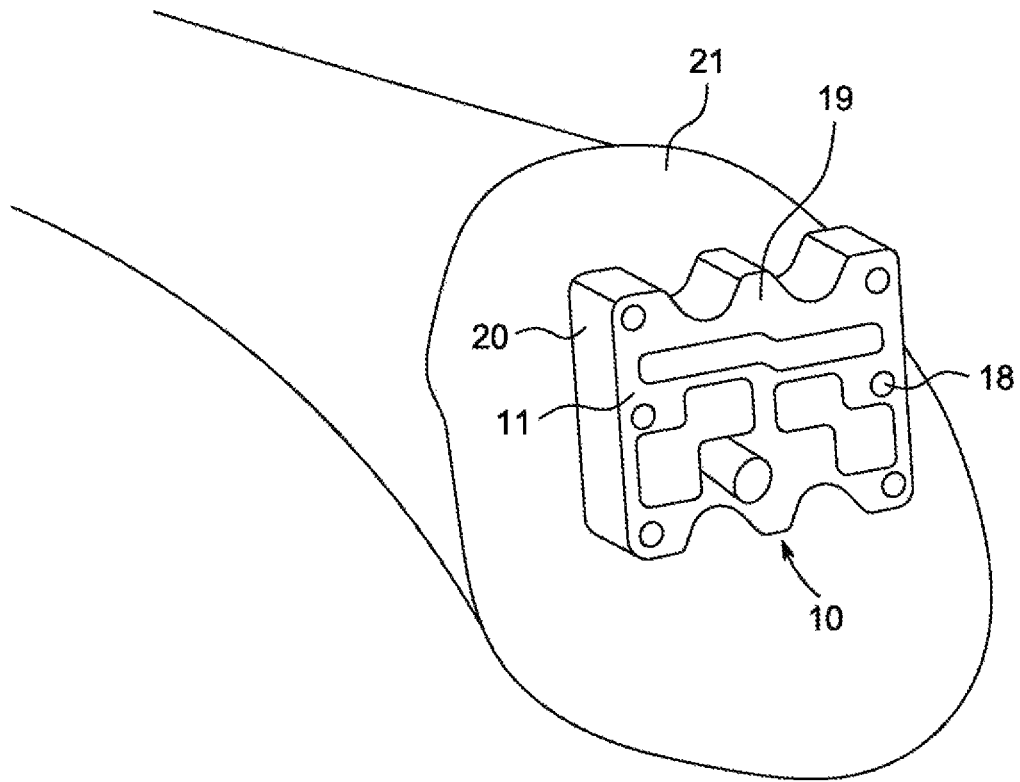
FIG. 3 is a view of the present jig member placed against a femur.

With reference to the present disclosure and in particular the attached figures, use of terminology relating to body planes is used. FIG. 1 depicts the various planes of a body. The sagittal plane 1 extends down through the body, dividing the body into left and right portions. The coronal or frontal plane 2 is a plane running perpendicular to the sagittal plane 1 and divides the body into anterior and posterior (front and back) portions. The transverse plane 3 is a horizontal plane dividing the body into upper and lower portions.

Figure 6:
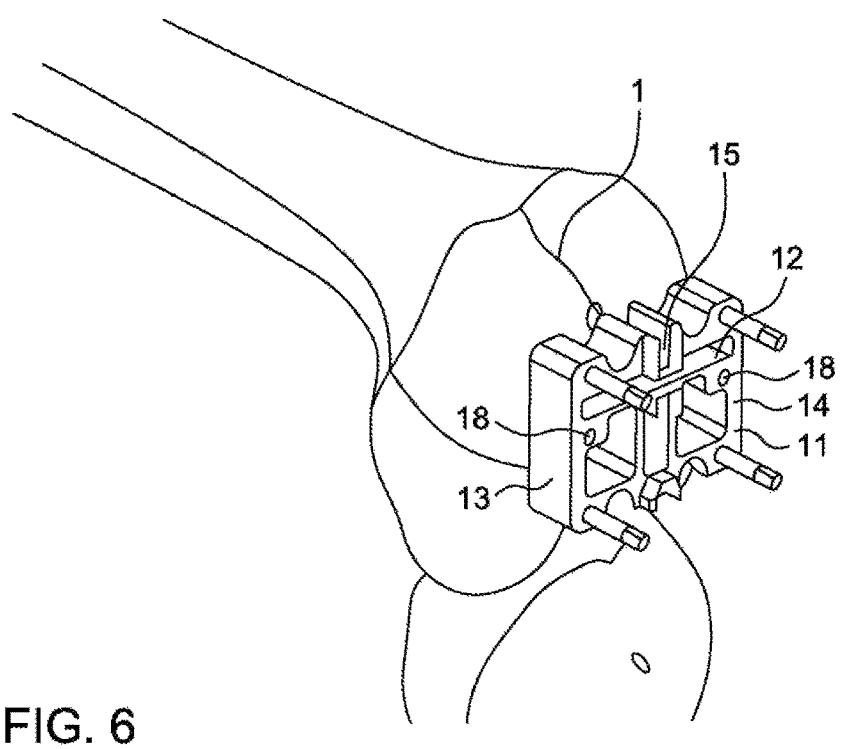
FIG. 6 is a further view of the jig member without the elongate arm attached.
Figure 7:
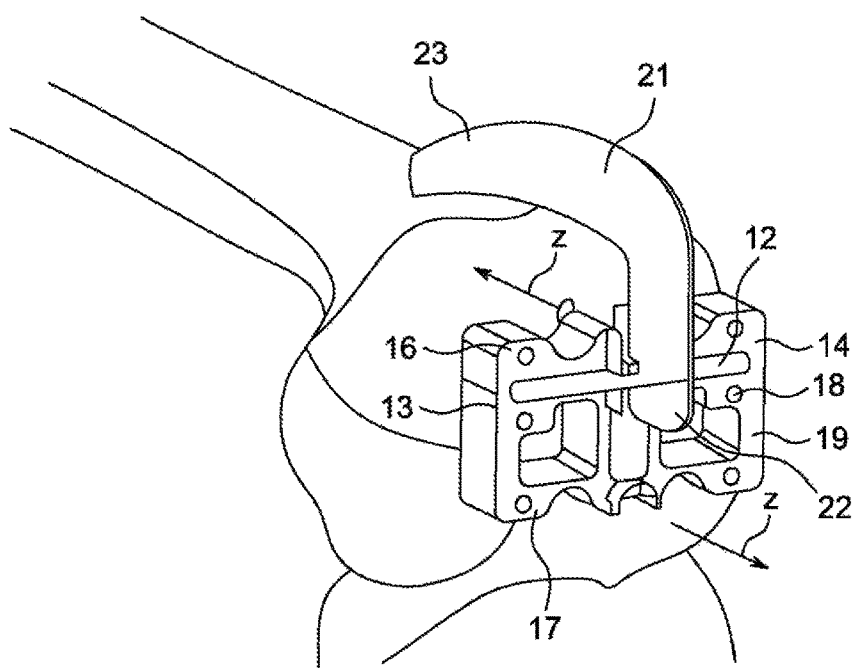
FIG. 7 is a view of the present jig member with the elongate arm attached.
Figure 8:
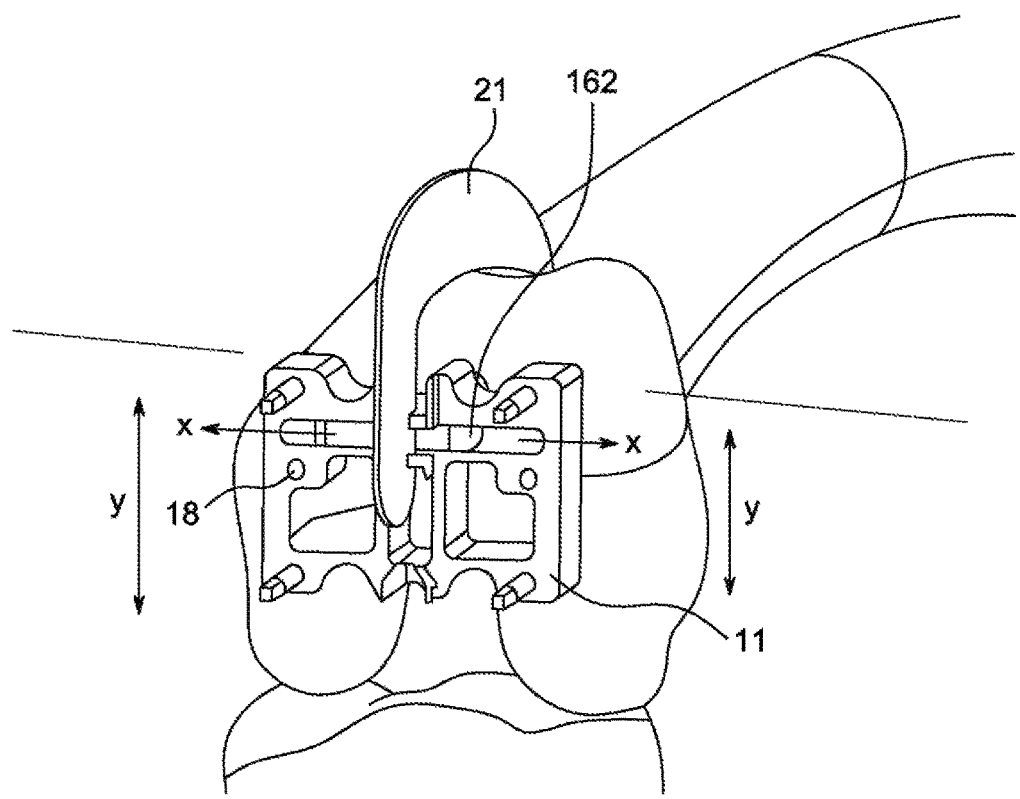
FIG. 8 shows the axes of movement of the jig member in situ.
Figure 9:
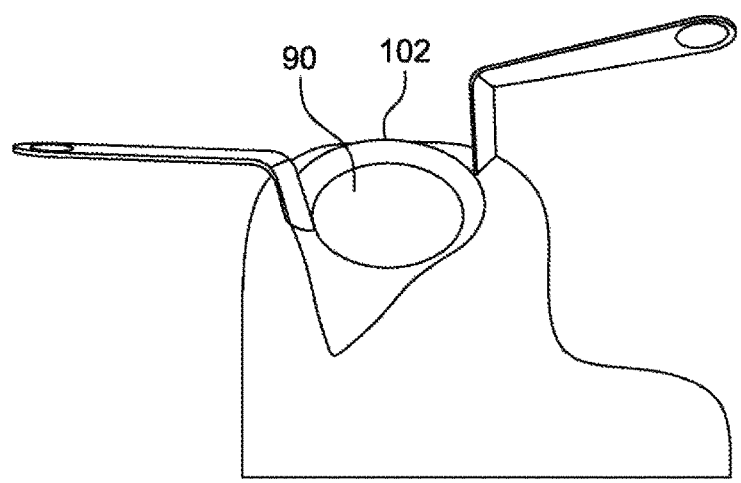
FIG. 9 is a schematic representation of a preliminary step in a knee replacement procedure.
Figure 10:
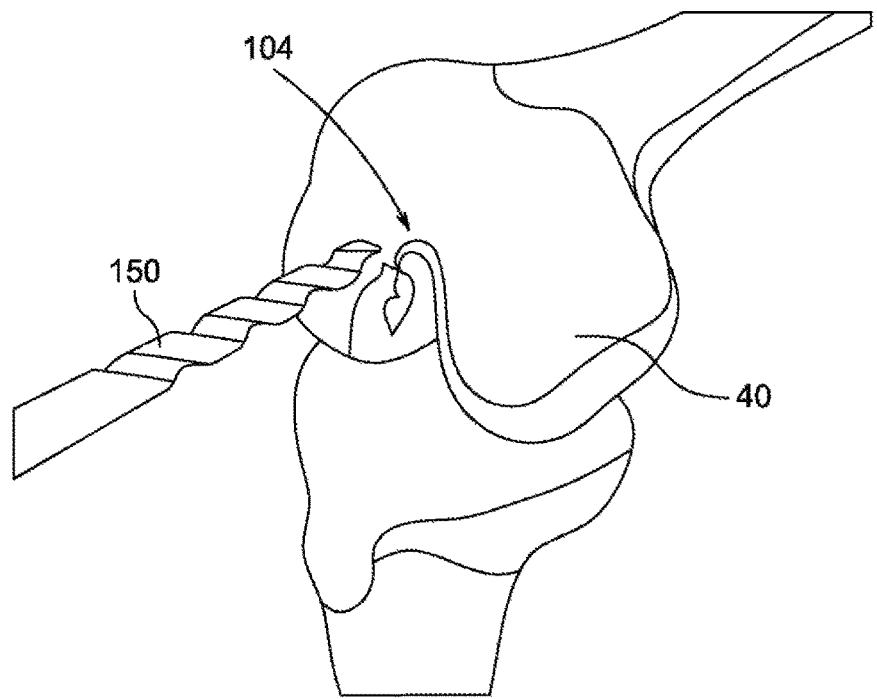
FIG. 10 is a schematic representation of a further step in a knee replacement procedure.
Figure 11:
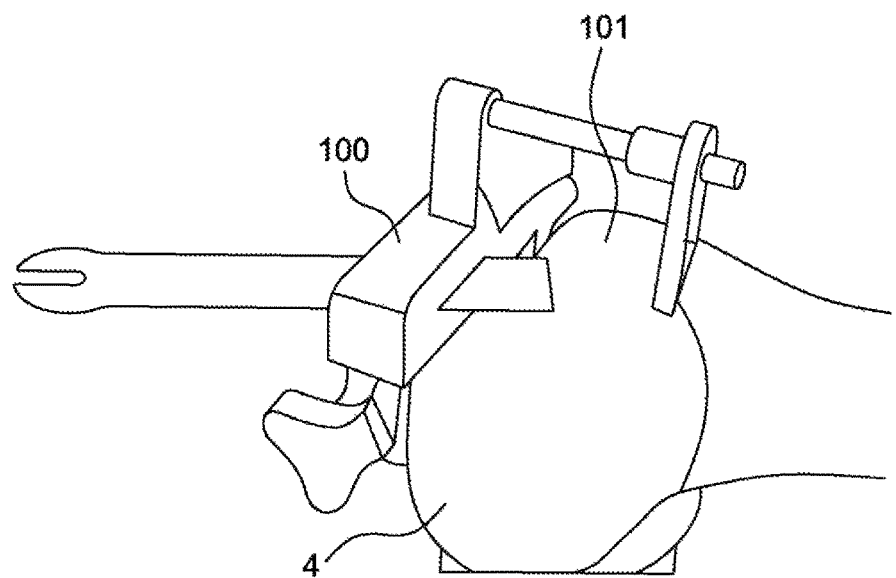
FIG. 11 shows an anterior femoral cutting block and the making of anterior cuts in the femur during a knee replacement procedure.
Figure 12:
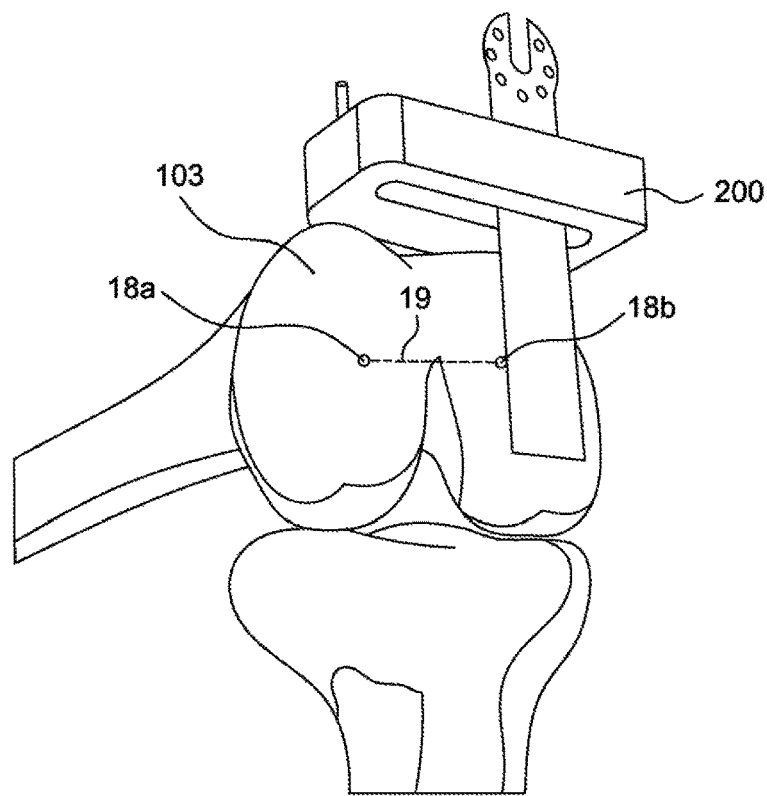
FIG. 12 shows a distal femoral cutting block and the making of the distal cuts on the femur of a patient.

The distal end of femur 4 comprises two condyles 5, separated from one another by a deep notch, the intercondylar notch 9. The condyles 5 are not exactly parallel with one another and each comprise an epicondyle 6 at an outer border. A line drawn between the two epicondyles 6 represents the trans-epicondylar axis (TEA) 7. Part of the Sulcus line 1 is also shown, for example in FIG. 6.

The present jig 10 is used to align and position cutting blocks for use in making surgical cuts in a bone of a patient. The jig comprises a main body 11 and a transverse slot 12 extending between a first sidewall 13 and a second 14 sidewall of the main body 11. A further horizontal slot 15 is provided which extends between a top portion 16 of main body to a lower portion 17 of main body 11

At least two drill holes 18 extend through the main body 11 from a rear face 19 to a bone engaging face 20 of main body 11.

The jig 10 further includes an elongate arm 21 which is removably attachable to the main body 11. Elongate arm 21 substantially arcuately extends from proximal end 22 to distal end 23 with a slight tapering towards the distal end 23. The shape of the elongate arm is configured to align with the Sulcus line 1 of the femur 4.

Specifically, jig 10 is used to align cutting blocks adjacent a distal femur 4. In one particular embodiment, jig 10 is used by a surgeon to align a cutting block 100 for making one or more anterior cuts 101 on the distal femur 4.

The depth and angle of the anterior cuts 101 has a bearing on the rotational alignment of a femoral component of a prosthetic knee system.

Steps in Knee Replacement Surgery:

In a knee replacement surgery, typically a surgeon makes an incision 102 across the front of the knee to gain access to the patella 90 and rotates the patella 90 outside the knee area. This allows the surgeon to view the femur 4 and size up the cuts necessary for inserting the various knee prosthesis components.

There are options as to which cut is made first but many surgeons prefer to make the distal femoral cut 103 first. However, before making any cut, it is important to size other cuts including the anterior femoral cut 101. This is especially the case if the surgeon is using the Sulcus line as a reference landmark since most of this line will be removed once the distal femoral cut 103 is made.

To perform the distal cut option, a broaching drill 150 drills into the medullary cavity of the femur 4, entering at the apex 104 of the intercondylar notch and up through the femur 4. The drill hole made is typically slightly oversized having around a 10 mm diameter compared to an intramedullary rod 160 which is typically around 8 mm in diameter. Such oversizing prevents pressurisation of intra-medullary fat during insertion of the intramedullary rod 160 and the consequent risk of fat embolism.

The intramedullary rod 160 is then inserted into the drilled hole and worked into the femoral medulla by hand. Proximal end 161 of intramedullary rod 160 extends outwardly from the femoral surface with the remainder of the length of rod 160 extending through the femur to align with the mechanical axis of femur 4.

Proximal end 161 comprises a flattened paddle 162 having an upper face 163 and an opposed lower face (not shown). The height 165 of paddle member 162 is sized such that it is received in transverse slot 12 of main body 11. The sizing of the transverse slot 12 and the paddle member 162 is such that the main body 11 of jig 10 may be relatively easily inserted over the paddle member 162. That is, the height 165 of paddle 162 is slight less than the height of transverse slot 12 of main body 11.

The intramedullary rod 160 is used to set the sagittal and coronal alignment of the distal cut of femur 4. It also sets the depth of the cut which is typically about 10 mm deep although it may be as little as 8 mm or up to 12 mm.

Before cutting any bone, it is important to set the rotational alignment. In the present disclosure, jig 10 allows the use of the Sulcus line 1 as a suitable landmark. With the main body of the jig positioned on the intramedullary rod 160, essentially the view of this line is substantially fixed in the sagittal plane. This avoids errors in translation of the Sulcus line 1 to a horizontal line which may result from the angle of view the surgeon has of the Sulcus line.

Elongate arm 21 is connected to main body 11 by sliding it into horizontal slot of main body 11. Once secured relative to the main body, a surgeon may line up the elongate arm 21 with their view of the Sulcus line 1. Because paddle 162 is transversely moveable within transverse slot 12, the main body may be moved in a transverse direction, shown by arrows (x) according to positioning of the elongate arm 21. Further, the intramedullary rod 160 is substantially rotatable in the coronal plane and therefore, once positioned on paddle 162, main body 11 is similarly rotatable as shown by arrows (y).

Importantly, however, the jig main body 11 is not flexed or extended in the sagittal plane as represented by arrows (z). This prevention of sagittal movement fixes the surgeons view of the Sulcus line 1 in this plane.

Once the elongate arm 21 is aligned, the position of main body 11 is fixed relative to the femur 4 by pinning it to the femur 4. Next, two pins (not shown) are inserted through holes 18 and drilled into the bone to form pin tracks 18a and 18b. Such drilling forms a track into the bone to a distal point. The pins may then be removed from the bone.

The jig 10 is removed from the intramedullary rod 160 and a distal femoral cutting block 200 positioned onto the anterior surface of the femur 4. The intramedullary rod 160 is then removed and a distal cut made through the distal femoral cutting block 200. By making this cut, a large portion of the Sulcus line 1 is removed but having tracked pins through pin holes 18, pin tracks 18a and 18b are still visible to the surgeon. A line 19 drawn between 18a and 18b is representative of the TEA 7 and may be used to correctly align an anterior femoral cutting block.

The distal femoral cutting block 200 is then removed.

In addition to referencing the Sulcus line 1, a surgeon may set femoral component rotation using the posterior condylar axis 28 (typically 3° of external rotation is routinely added to the posterior condylar axis).

An advantage of this is that a surgeon may then use the posterior condylar axis 28 to directly compare with the line between 18a and 18b made using jig 10. The average may then be taken from referencing the posterior condylar axis 28 and the line drawn between 18a and 18b to set the rotational alignment of the femoral component.

An anterior cutting block 100 of the correct size is then pinned in position on the bone, at the correct angle relative to the pin tracks 18a and 18b and any other marker used, and the anterior cuts 101 made.

Figure 13:
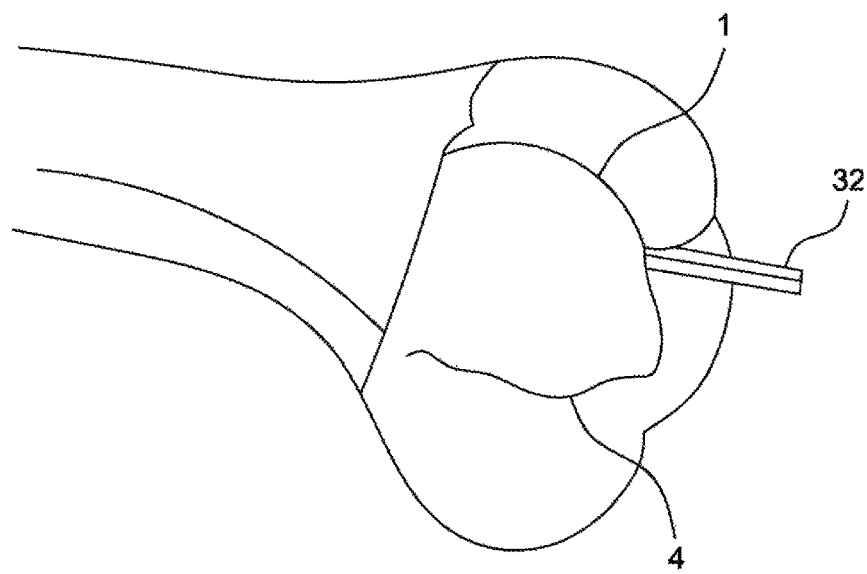
FIG. 13 is a schematic representation of a distal end of a femur with a pin inserted by computer navigation.
Figure 14:
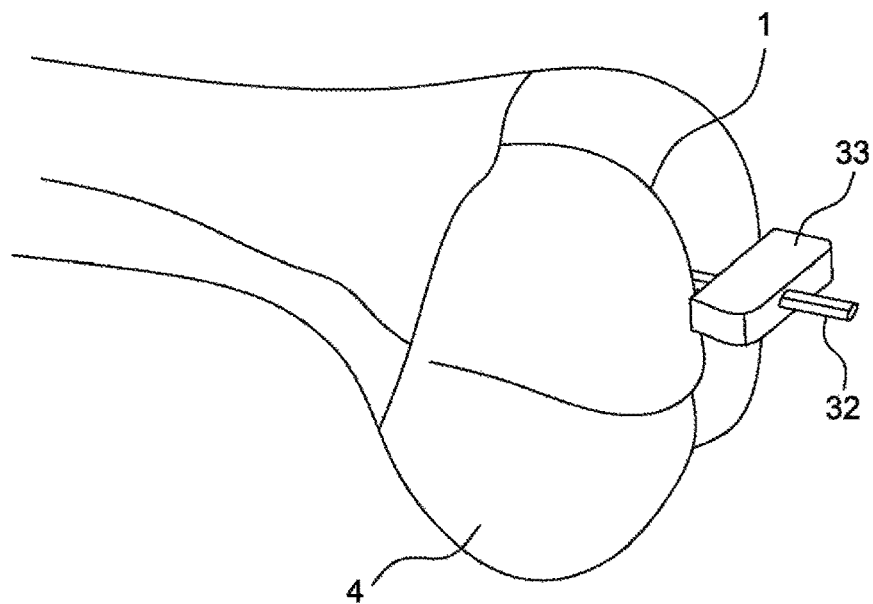
FIG. 14 shows a paddle member inserted over the pin of FIG. 13.
Figure 15:
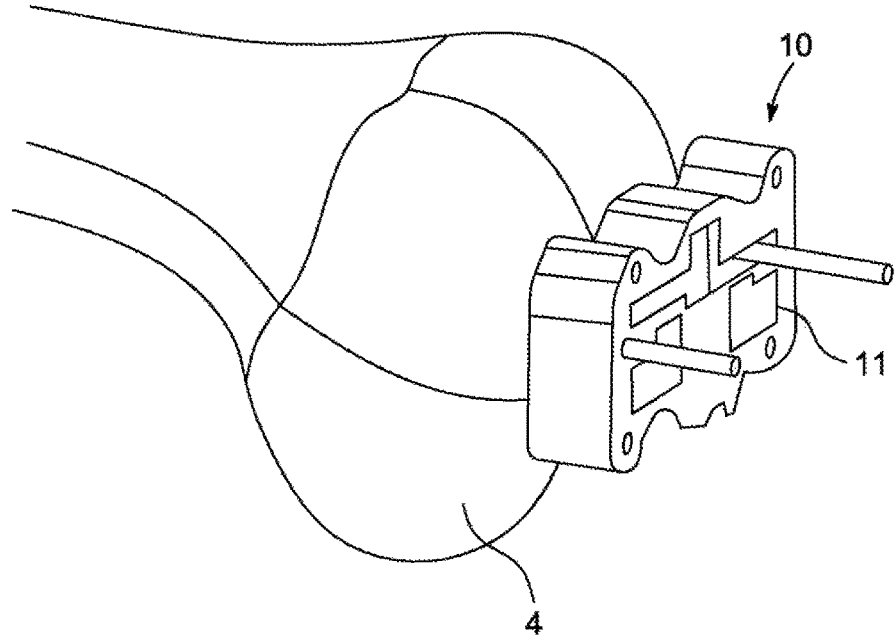
FIG. 15 shows the present jig member attached to the pin and paddle of FIGS. 13 and 14.

In a further embodiment, the jig member 10 of the present disclosure may be used with a computer navigation system. Part of this method is shown in FIGS. 13 to 15. A central pin 32 is inserted into the centre of the knee instead of the intramedullary rod 160 using computer assisted navigation. A paddle member 33 which has a hole therein, is slid onto the central pin 32. Jig 10 is then placed over the paddle member 33 in much the same manner as described above using the intramedullary rod.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A surgical alignment system for use in positioning of a prosthetic component on or in a bone of a subject; said system including:
    an intramedullary member; and
    a jig member including a main body that has a transverse and a longitudinal axis and a transversely extending slot therein to receive a portion of the intramedullary member, the jig member further including an elongate arm which comprises a first end connected to the main body and wherein the elongate arm is configured to align with a bony landmark of said bone;
    wherein when the portion of the intramedullary member is received in the transversely extending slot of the jig member, the jig member is (i) moveable transversely relative to the intramedullary member and (ii) rotatable in a first plane, parallel to a coronal plane, relative to the intramedullary member to substantially align the elongate arm with the bony landmark; and
    wherein when the portion of the intramedullary member is received in the transversely extending slot of the jig member, the jig member is substantially fixed in a second plane, parallel to a sagittal plane, relative to the intramedullary member.

2. The surgical alignment system of claim 1, wherein the main body of the jig member has a bone facing surface and an opposite surface, the main body including at least two holes therein.

3. The surgical alignment system of claim 2, wherein the holes are configured to receive a pin or screw therein to mark holes in the bone of the subject.

4. The surgical alignment system of claim 1, wherein the bony landmark comprises the Sulcus line on a femur of a subject.

5. The surgical alignment system of claim 1, wherein, the elongate arm comprises an arcuate body which extends from the first end connected to the main body of the jig member to a distal end.

6. The surgical alignment system of claim 5 wherein the elongate arm tapers in width along its length from the first end to the distal end.

7. The surgical alignment system of claim 1, wherein the elongate arm is removably connected to the main body of the jig member.

8. The surgical alignment system of claim 1, wherein the main body of the jig member comprises a first elongate slot configured to receive a proximal portion of the elongate arm adjacent to the first end of the elongate arm.

9. The surgical alignment system of claim 8, wherein the first elongate slot extends parallel to the longitudinal axis of the main body.

10. The surgical alignment system of claim 1, wherein the intramedullary member comprises an elongate member which extends from a proximal end to a distal end and wherein said distal end is configured for introduction into a bone and said proximal end is configured to extend outwardly from said bone.

11. The surgical alignment system of claim 10, wherein the proximal end of the intramedullary member comprises a substantially flattened end.

12. The surgical alignment system of claim 1, wherein the intramedullary member is substantially rotatable in the first plane, parallel to a coronal plane, relative to a bone in which at least its distal end is inserted such that when the portion of the intramedullary member is received in the transversely extending slot of the jig member, rotatable movement of the intramedullary member causes the main body to also rotate in the first plane.

13. A method for positioning a prosthetic component on or in a bone of a subject, said method including:
   inserting an intramedullary member into the bone;
   providing a jig member including a main body that has a transverse axis, a longitudinal axis, and a transversely extending slot therein, the jig member further including an elongate arm having a first end that is connected to the main body of the jig member;
   connecting the jig member to said intramedullary member such that a portion of the intramedullary member is received in the transversely extending slot of the main body of the jig member, the step of connecting the jig member to the intramedullary member substantially fixing the jig member relative to the intramedullary member in a first plane, parallel to a sagittal plane; and
   aligning the elongate arm with a bony landmark wherein the jig member is (i) moveable transversely relative to the intramedullary member and (ii) rotatable in a second plane, parallel to a coronal plane, relative to the intramedullary member to substantially align the elongate arm with the bony landmark as the elongate arm is aligned with the bony landmark.

14. A surgical alignment system for use in positioning of a prosthetic component on or in a bone of a subject, said system for use with a computer assisted navigation alignment system and including:
   a bone marker member; and
   a jig member including a main body that has a transverse axis, a longitudinal axis, and a transversely extending slot therein to receive a portion of the bone marker, said jig member further including an elongate arm having a first end that is connected to the main body of the jig member, the elongate arm configured to align with a bony landmark of said bone;
   wherein when the portion of the bone marker is received in the transversely extending slot of the jig member, the jig member is moveable transversely relative to the bone marker and is further rotatable in a plane parallel to a coronal plane, relative to the bone marker member to substantially align the elongate arm with the bony landmark.

* * * * *